United States Patent [19]
Notomi

[11] Patent Number: 5,348,471
[45] Date of Patent: Sep. 20, 1994

[54] LOWER JAW MOVING FUNCTION READJUSTING APPARATUS AND POSITION DETERMINATION SETTING APPARATUS

[76] Inventor: Tetsuo Notomi, 1-14-15, Kakinokizaka, Meguroku, Tokyo, Japan

[21] Appl. No.: 966,012

[22] Filed: Oct. 23, 1992

[51] Int. Cl.⁵ .............................................. A61C 11/00
[52] U.S. Cl. .................................... 433/57; 433/56
[58] Field of Search ........................ 433/54, 55, 56, 57, 433/58, 59

[56] References Cited

U.S. PATENT DOCUMENTS

| | | | |
|---|---|---|---|
| 1,670,311 | 5/1928 | Musante | 433/55 |
| 2,043,394 | 6/1936 | Reith | 433/58 |
| 2,884,696 | 5/1959 | Bonfanti | 433/57 |
| 3,423,834 | 1/1969 | Irish | 433/56 |
| 5,160,262 | 11/1992 | Alpern et al. | 433/57 |

FOREIGN PATENT DOCUMENTS

| | | | |
|---|---|---|---|
| 364815 | 12/1922 | Fed. Rep. of Germany | 433/55 |
| 176705 | 3/1922 | United Kingdom | 433/55 |

*Primary Examiner*—Cary E. O'Connor
*Attorney, Agent, or Firm*—Oblon, Spivak, McClelland, Maier & Neustadt

[57] ABSTRACT

A lower jaw moving function readjusting apparatus, which includes: an upper and lower triangular shaped plate; a front receiving tray and two rear receiving trays fixedly mounted on the triangular shaped lower plate, a front scribing needle and two rear scribing needles, each of which has a lower end which is positioned in hardenable material located in each of the front and rear receiving trays. The needles are suspended from the upper support plate and the height of at least one of the needles is adjustable. The upper and lower springs are hinged together so as to be pivotably opened or closed and the upper springs and lower springs are secured, respectively, to the upper and lower support plates.

6 Claims, 7 Drawing Sheets

LOWER JAW MOVING FUNCTION READJUSTING APPARATUS AND POSITION DETERMINATION SETTING APPARATUS

BACKGROUND OF THE INVENTION

1. Field of the Invention

The present invention relates to a lower jaw moving function readjusting apparatus and a position determination setting apparatus employable for the first-mentioned apparatus.

2. Description of the Prior Art

Figure 10:
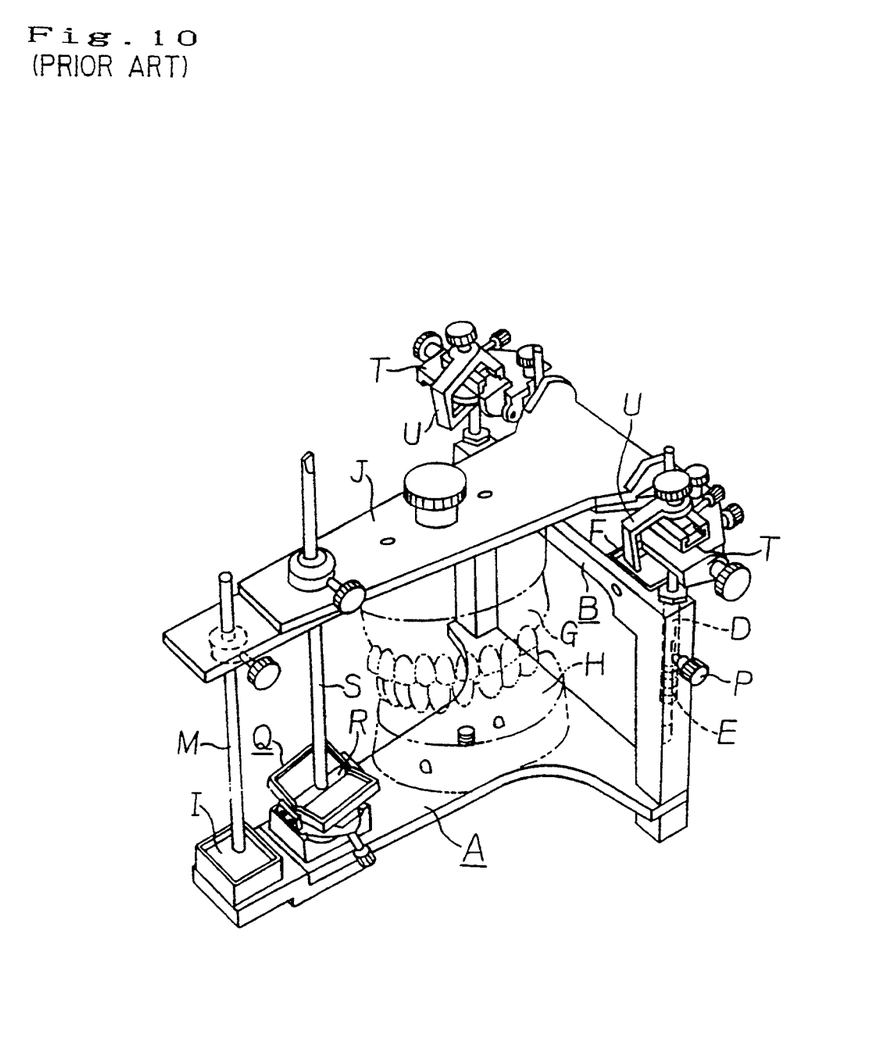
FIG. 10 is a perspective view of a conventional functional occluding apparatus.
Figure 11:
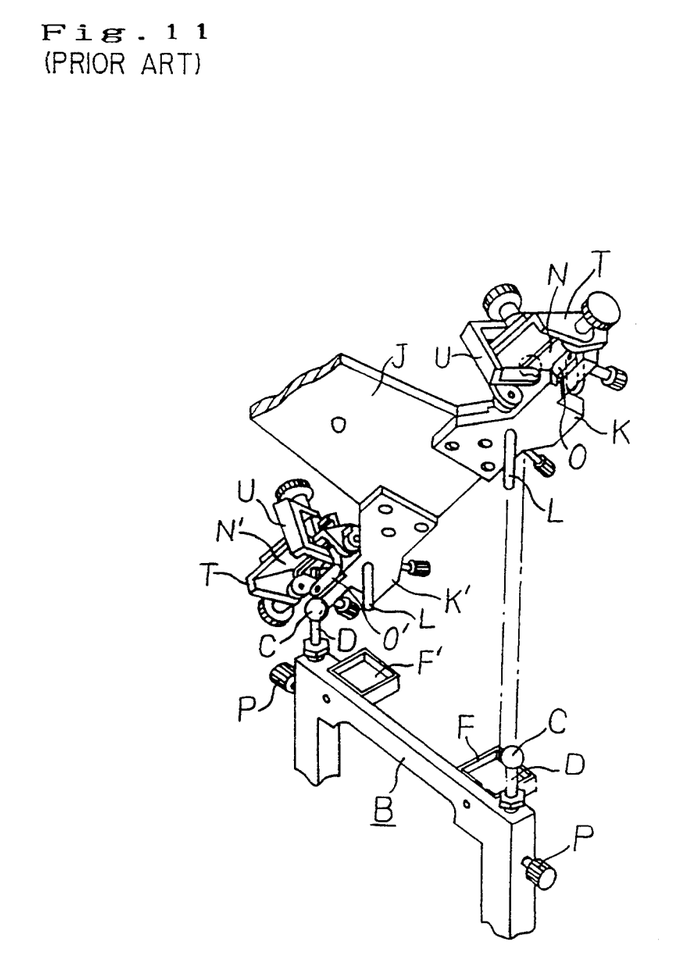
FIG. 11 is a fragmentary perspective view of the conventional functional occluding apparatus shown in FIG. 10, particularly illustrating essential components therefor in the disassembled state.

A functional occluding apparatus proposed by a common inventor to the present invention and a corresponding patent filed by him as Japanese Publication Patent No. 51-42874 is filed shown in FIG. 10 and FIG. 11.

Specifically, the functional occluding apparatus includes a base board A on which a lower jaw model H is fixedly mounted, and a gate-shaped supporting member B immovably stands upright from the right-hand end of the base board A. A pair of spherical headed support rods D each having a spherical head C corresponding to a condyle placed on the top end thereof are normally biased in the upward direction from the opposite ends of the gate-shaped supporting member B by the resilient force of coil springs E. A pair of tray-shaped boards F and F′ each to be filled with a quick hardenable material are placed on the opposite ends of the gate-shaped supporting member B, and another tray-shaped board I is placed on the left-hand end of the base board A. In addition, the functional occluding apparatus includes a turnable frame J for fixedly holding an upper jaw model G, and a pair of styluses L and L′ are suspended from holding pieces K and K′ on the opposite ends of the turnable frame J, while another stylus M is suspended from the foremost end of the turnable frame J. The holding pieces K and K′ have engagement spaces N and N′ on the lower sides thereof so as to allow the spherical heads C to be engaged with the engagement spaces N and N′. With this construction, when the turnable frame J is turnably displaced to the region where molar teeth on upper and lower front teeth occlude each other at the central part thereof, the results derived from the occlusion of the fore-teeth at the central parts of the upper and lower jaws are expressively reproduced on the quick hardenable material filled in the tray-shaped boards F, F′ and I.

With respect to the region where molar teeth on upper and lower rear-teeth occlude each other at the central part thereof, turnable distance pieces O and O′ adapted to turn in the engagement spaces N and N′ are turnably suspended from the latter so as to enable the spherical heads C to be displaced in the rearward direction while the engagement spaces N and N′ are widened, whereby the results derived from the occlusion of the rear-teeth at the central parts of the upper and lower jaws are likewise expressively reproduced on the quick hardenable materials in the tray-shaped boards F, F′ and I by the styluses L, L′ and M in synchronization with the occlusion of the fore-teeth as mentioned above.

In case the styluses L, L′ and M move in excess of the aforementioned movement range, while the spherical headed holding rods D are fixedly held by tightening screws P, each movement of the styluses L, L′ and M is properly guided by an inclinable projection R in a guiding unit Q disposed in the vicinity of the tray-shaped board I, another stylus S, inclination boards T disposed in the engagement spaces N and N′, a guiding piece U and the spherical heads C.

In contrast with the prior functional occluding apparatus, the conventional functional occluding apparatus constructed in the above-described manner makes it possible to expressively reproduce not only the region where molar teeth on the upper and lower fore-teeth occlude each other at the central part thereof but also the region where molar teeth on the upper and lower rear-teeth occlude each other at the central part thereof. With respect to the range in excess of the aforementioned regions, however, the conventional functional occluding apparatus can not properly expressively reproduce practical movement of a patient's lower jaw merely by detecting the movement of the teeth on the upper and lower jaws in the form of two-dimensional displacement of them on a single plane, although this plane can freely be inclined.

SUMMARY OF THE INVENTION

The present invention has been made in consideration of the foregoing background and its object resides in providing a lower jaw moving function readjusting apparatus which assures that the movement of a lower jaw can correctly be expressed by enabling an upper support plate for fixedly holding an upper jaw model to be freely displaced.

To accomplish the above object, according to one aspect of the present invention, there is provided a lower jaw moving function readjusting apparatus which is constructed such that a front receiving tray and two rear receiving trays are fixedly mounted on a triangle-shaped power support plate; a front scribing needle and two rear scribing needles each of which lower end is immersed in a quick hardenable material filled in each of the front and rear receiving trays are immovably suspended from an upper support plate arranged opposite to the lower support plate while their heights are properly adjusted; and upper springs and lower springs adapted to be turnably opened or closed to turn about a hinge are secured to the upper and lower support plates on the opposite sides of the latter.

In addition, the lower jaw moving function readjusting apparatus is constructed such that a substantially U-shaped spring joint tube of which upper side is kept open and an inverted substantially U-shaped spring joint tube of which lower side is kept open are pivotally secured to the hinge; and one of each of the upper springs a single vertical turn are fitted into the opposite ends of the upper spring joint tube and the other end of the same are held by the upper support plate on the opposite sides of the latter, while one end of each of the lower springs having a single horizontal turn are fitted into the opposite ends of the lower spring joint tube and the other ends of the same are held by the lower support plate at the opposite ends of the latter.

Additionally, the lower jaw moving function readjusting apparatus is constructed such that each of the upper and lower support plates is designed with a substantially triangular contour; the upper spring support tube and the lower spring support tube are turnably held while extending along the longer side of the triangular contour; and one ends of the upper springs and the lower springs are fitted into the opposite ends of the upper spring support tube and the lower spring support tube.

Further, the lower jaw moving function readjusting apparatus is constructed such that an arc-shaped guide wall is projected forward of the front receiving tray located at the fore end part of the lower support plate; an adjusting board having a series of calibrations formed along an arc is disposed on the fore receiving tray side; two sector-shaped adjustment pieces adapted to move along the guide wall and then fixedly secured to the same are placed on the adjustment board; and in addition to the fore scribing needle, a position determining rod normally biased in the downward direction by the resilient force of a spring and having a plurality of calibrations formed at the upper end part thereof is suspended from a holding piece such that the lower end of the position determining rod is properly brought in contact with the adjustment board while the position of the position determining rod is properly adjusted on the adjustment board in the upward/downward direction as well as in the leftward/rightward direction and then fixed thereon.

According to another aspect of the present invention, there is provided a position determination setting apparatus employable for the lower jaw moving function readjusting apparatus which is constructed such that the position determination setting apparatus comprises a position determining unit of which upper surface has a trapezoidal contour and an occlusion plane plate wherein the position determining unit has a central guide groove formed thereon while extending between the opposite parallel sides of the trapezoidal contour and includes fitting portions adapted to be fitted to the lower spring support tubes on the lower support plate in cooperation with key-shaped engagement pieces, while the occlusion plane plate includes a pair of tongue pieces each having a modeling compound deposited thereon, each of the tongue pieces having a plurality of impressions formed thereon corresponding to teeth on an upper jaw adapted to come in occlusive contact with teeth on the upper jaw model, and moreover, two front and rear guide pins of which lower ends are fitted into the central guide groove and of which upper ends are projected upward from the occlusion plane plate in alignment with a median seam line on the upper jaw model so as to allow the guide pins to be located at the central positions between the impressions formed on the deposited modeling compounds.

Moreover, the position determination setting apparatus employable for the lower jaw moving function readjusting apparatus is constructed such that two connection pieces are bridged between the tongue pieces on the occlusion plane plate while forming a groove therebetween; another groove is formed in the vicinity of the terminal ends of the tongue pieces; a stopper having a relatively large diameter is disposed at the intermediate position of each of the front and rear guide pins so as to allow the stopper to be placed on each of the grooves while the front and rear guide pins are fitted into both the grooves; and lock nuts are threadably engaged with male-threaded portions of the front and rear guide pins.

According to the present invention, with the lower jaw moving function readjusting apparatus constructed in the above-described manner, the upper support plate is turnably opened by upward turning movement about the hinge so that an upper jaw model is fixedly mounted on the upper support plate and a lower jaw model is fixedly mounted on the lower support plate. Subsequently, a quick hardenable material is filled in the fore receiving tray, and the upper and lower jaw models are then brought in occlusion with each other. Thereafter, the upper support plate is displaced in the forward direction as well as in the leftward/rightward direction against the resilient force of the upper springs and the lower springs so that the displacement of the upper support plate is recorded on the quick hardenable material by the front scribing needle to form a path for the movement of a lower jaw. On completion of the recording operation, the quick hardenable material is hardened.

Subsequently, a hardenable material is filled in each of the rear receiving trays, and the upper support plate is then displaced in the forward direction as well as in the leftward/rightward direction in the same manner as mentioned above. Thereafter, the results derived from the displacement of the upper support plate are recorded on the quick hardenable materials by both the rear scribing needles. On completion of the recording operation, the quick hardenable materials are hardened.

Next, artificial teeth are inserted into damaged or broken parts on the upper and lower jaw models and the path for the movement of the lower jaw on the quick hardenable materials is then followed by the fore scribing needle and the rear scribing needles so that practical occlusive movement of the patient's teeth is exactly reproduced, resulting in collision marks appearing on incorrect spots on the artificial teeth. Thus, the artificial teeth completely suitable for patient can be obtained with the lower jaw moving function readjustment apparatus.

In addition, since each of the lower springs has a single horizontal turn and each of the upper springs has a single vertical turn, the displacement of the upper support plate in the forward direction, in the leftward/rightward direction and in the upward/downward direction can be sufficiently achieved.

In case that an adjustment board is additionally used for the lower jaw moving function readjustment apparatus, as the position determining rod is displaced while the upper support plate is displaced in the leftward/rightward direction, adjustment pieces are displaced to come in contact with the position determining rod and then fixed on the adjustment board. At this time, the position of one adjustment piece located on the correct side is visually read with reference to the corresponding calibration on the position determining rod so that the other adjustment piece is displaced to positionally coincide with the foregoing calibration, whereby the path for the movement of a lower jaw on the quick hardenable material is adjustably positioned with a symmetrical relationship as seen in the leftward/rightward direction.

In addition, the position determination setting apparatus is constructed such that the fitting portions in the position determining unit are fitted to the lower spring support tube on the opposite sides thereof to determine their positions and the front and rear guide pins held on the occlusion plane plate are then fitted into both the grooves so that the front and rear guide pins are exactly aligned with a median seam line on the upper jaw model. While the foregoing state is maintained, the upper jaw model is mounted on the upper support plate so as to allow it to be set at the correct position.

Subsequently, the position determining unit and the occlusion plane plate are removed from the assembled structure, and the lower jaw model is fixedly mounted on the lower support plate in such a manner that it is brought in occlusion with the upper jaw model.

It should be noted that the fore and rear guide pins are displaced along both the grooves corresponding to the positions of impressions formed on the modeling compounds to determine their positions, and thereafter, they are fixedly secured to the occlusion plane plate.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DESCRIPTION OF THE PREFERRED EMBODIMENTS

Figure 1:
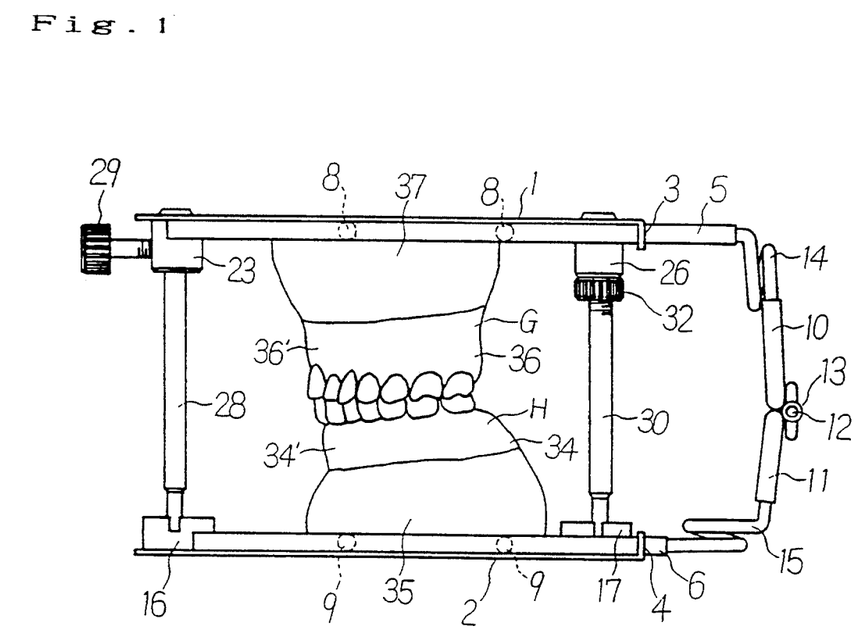
FIG. 1 is a side view of a lower jaw moving function readjusting apparatus in accordance with a first embodiment of the present invention.
Figure 2:
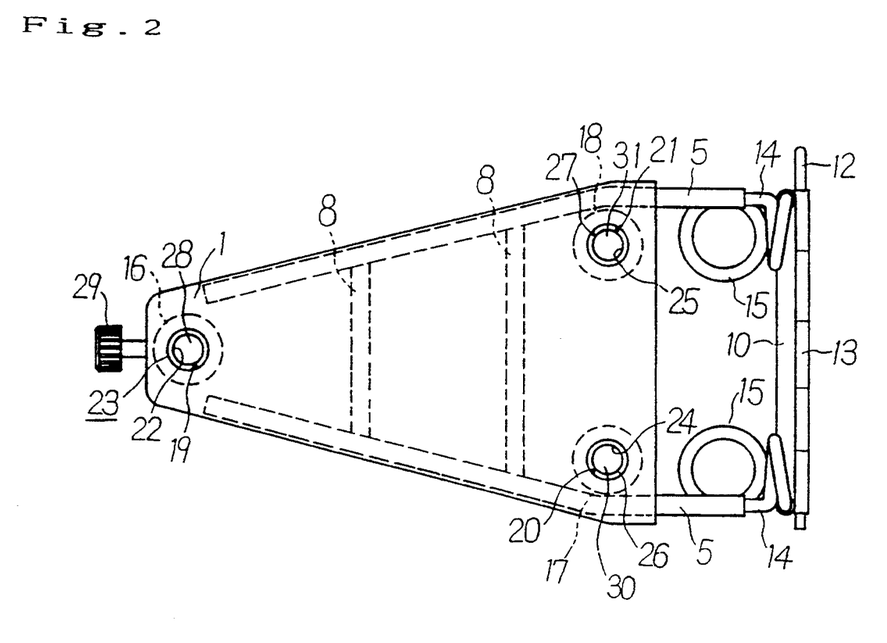
FIG. 2 is a plan view of the lower jaw moving function readjustment apparatus shown in FIG. 1.
Figure 3:
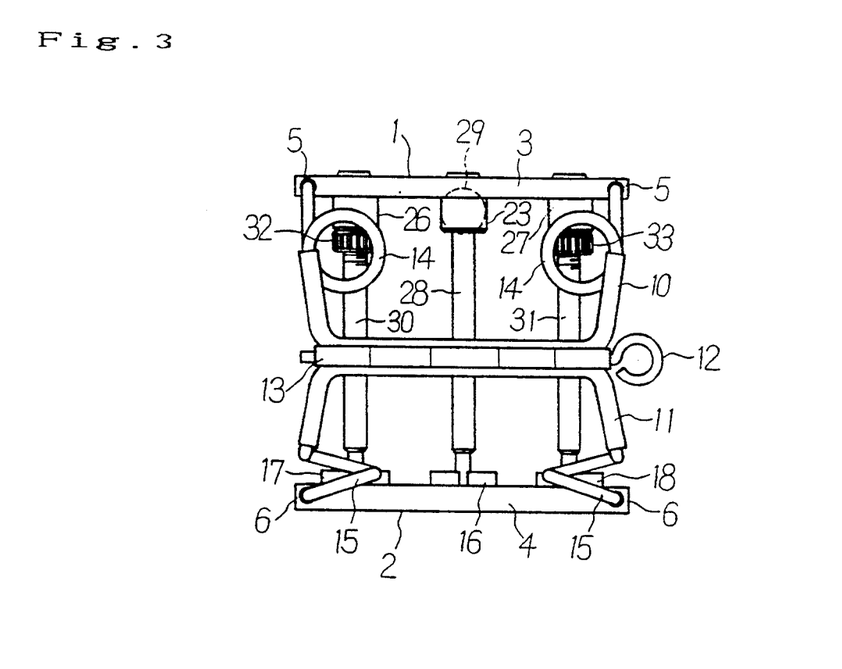
FIG. 3 is a rear view of the lower jaw moving function readjusting apparatus shown in FIG. 1 as seen from the rear side.
Figure 4:
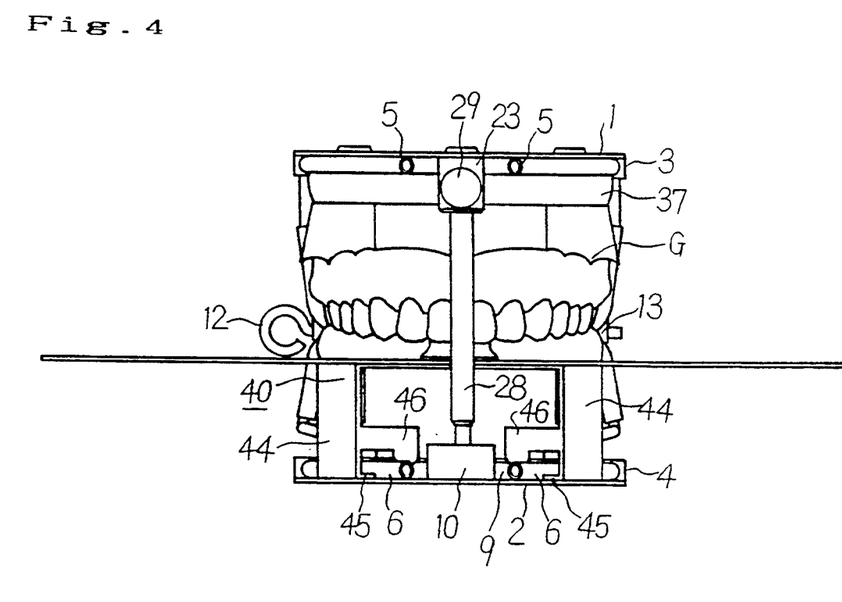
FIG. 4 is a front view of the lower jaw moving function readjusting apparatus shown in FIG. 1 wherein a position determination setting apparatus is secured to the lower jaw moving function readjusting apparatus.
Figure 5:
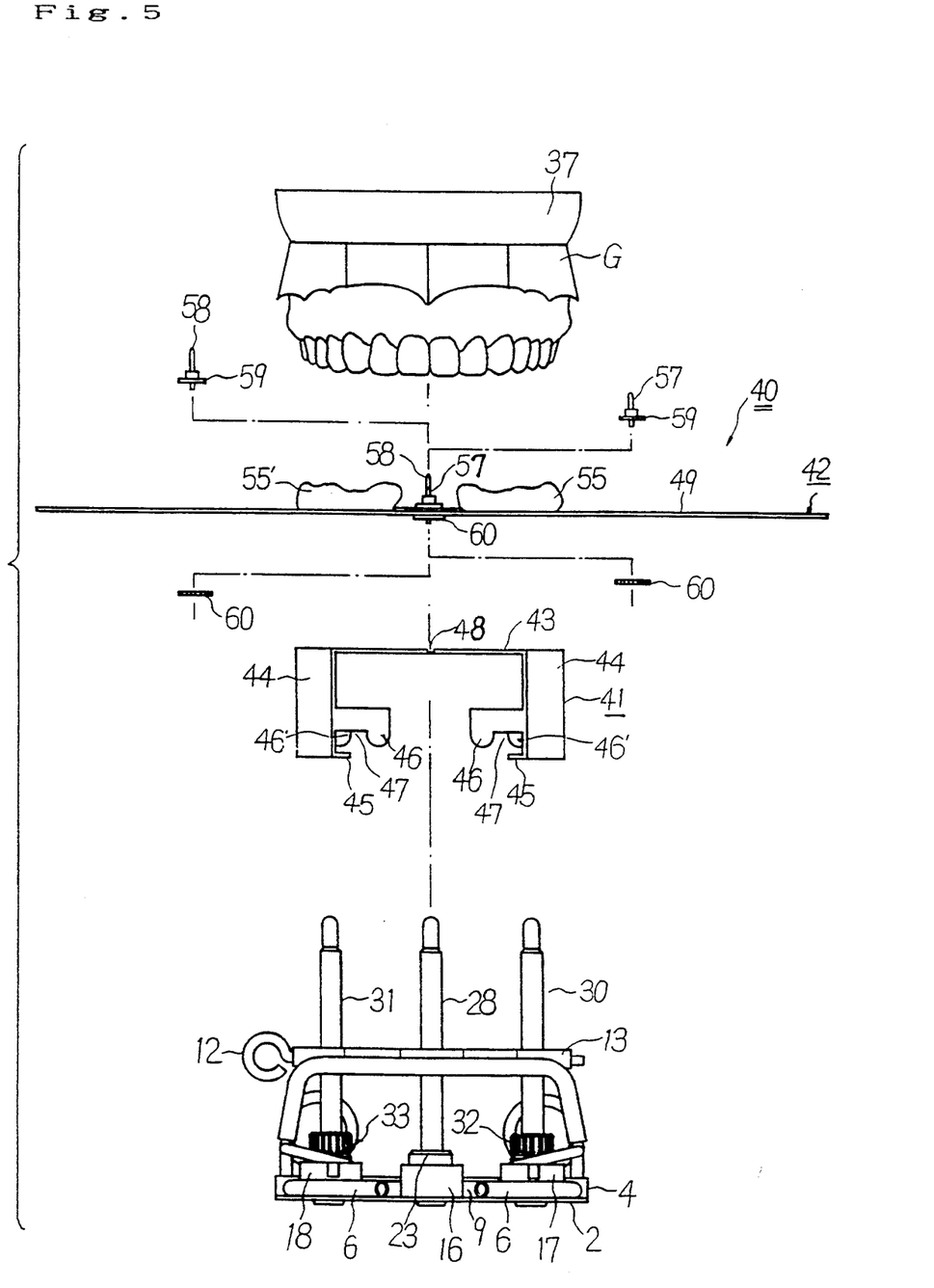
FIG. 5 is a front view of the lower jaw moving function readjusting apparatus shown in FIG. 1 particularly illustrating in the disassembled state that an upper support plate is removed therefrom by upward turning movement of the upper support plate about a hinge.

The present invention will now be described in detail hereinafter with reference to FIG. 1 to FIG. 3 which show a lower jaw moving function readjusting apparatus in accordance with a first embodiment of the present invention. The apparatus includes upper and lower triangle-shaped support plates 1 and 2 which are located opposite to each other and of which corner portions are exploded for the purpose of facilitating illustration of the apparatus. Projections 3 and 4 are arranged in the opposing relationship in the regions corresponding to one side of each of the upper and lower support plates 1 and 2. In addition, upper spring support tubes 5 extend along the opposite sides of the upper support plate 1 past the projection 3 to reach the positions in the vicinity of an apex (hereinafter referred to as a foremost end) of the upper support plate 1, while lower spring support tubes 6 extend along the opposite sides of the lower support plate 2 past the projection 4 to reach the positions in the vicinity of the foremost end of the lower support plate 2. It should be added that the upper and lower support tubes 5 and 6 are fixedly secured to the upper and lower support plates 1 and 2. Two reinforcement rods 8 are bridged between the upper spring support tubes 5 for the purpose of reinforcement, while two reinforcement rods g are bridged between the lower spring support tubes 6 for the same purpose.

A U-shaped spring joint tube 10 is arranged while it is kept open in the upward direction, while an inverted U-shaped spring joint tube 11 is arranged while it is kept open in the downward direction. Both the spring joint tubes 10 and 11 are fixedly jointed to a hinge 13 so as to allow them to turn about the latter. One ends of each of the upper springs 14 having a single vertical turn are fitted into the upper spring joint tube 10, while the other ends of the same are fitted into the upper spring support tubes 5. On the other hand, one ends of each of the lower springs 15 each having a single horizontal turn are fitted into the lower spring joint tubes 11, while the other ends of each of the same are fitted into the lower spring support tubes 6. With this construction, the upper and lower support plates 1 and 2 are resiliently jointed to each other so that the upper support plate 1 can be displaced in the forward/rearward direction, in the leftward/rightward direction and in the upward/downward direction.

Three receiving trays 16, 17 and 18 are fixedly mounted at respective corners on the upper surface of the lower support plate 2. On the other hand, through holes 19, 20 and 21 are formed at respective corners of the upper support plate 1, and part of a front pin receiver 23 is fitted into the through hole 19 located at the fore end of the upper support plate 1 such that its upper surface is fixedly secured to the lower surface of the upper support plate 1. In addition, part of a rear pin receiver 26 having a female-threaded hole 24 formed thereon is fitted into the through hole 20 on the bottom side (i.e., rear end side) of the upper support plate 1 such that its upper surface is fixedly secured to the lower surface of the upper support plate 1. Similarly, part of a rear pin receiver 27 having a female-threaded hole 25 formed thereon is fitted into the through hole 21 on the lower surface of the upper support shaft 1 such that its upper surface is fixedly secured to the lower surface of the upper support plate 1. After the upper end of a front scribing needle 28 is fitted into the front pin receiver 23 while adjusting a height of the front scribing needle 28, a fixing male-threaded rod 29 is threadably fitted into a female threaded hole in the front pin receiver 23 so that the front scribing needle 28 is fixedly mounted on the receiving tray 16 in the upright standing state. The upper male-threaded ends of both the rear scribing needles 30 and 31 are threadably fitted into the female-threaded holes 24 and 25 of the rear pin receivers 26 and 27, and after a height of each of the rear scribing needles 30 and 31 is properly adjusted, they are fixedly mounted on the rear pin receivers 26 and 27 by threadably tightening lock nuts 32 and 33.

According to the first embodiment of the present invention, since the lower jaw moving function readjusting apparatus is constructed in the above-described manner, the upper support plate 1 can turned so as to be opened or closed relative to the lower support plate 2 by turning movement about the hinge 13. While the upper support plate 1 is kept open, a part 34' of a lower jaw 34, i.e., a patient's lower jaw model H is mounted on both the reinforcement rods 9 via a mounting anvil 35 and a part 36' of an upper jaw 36, i.e., a patient's Upper jaw model G is suspended from both the reinforcement rods 8 via a mounting anvil 37 such that the central parts of the upper and lower jaw models G and H are to be later correctly aligned with each other in the vertically occluded state.

Subsequently, a quick hardenable material (synthetic resin or the like) is filled in the front receiving tray 16 and the upper support plate 1 is turnably closed by downward turning movement about the hinge 12 so that both the upper and lower jaw models G and H occlude each other in the vertically aligned state, and thereafter, when they are displaced in the forward direction as well as in the leftward/rightward direction so as to allow them to slightly rub each other, the upper support plate 1 is displaced in the forward/rearward direction, in the leftward/rightward direction and in the upward/downward direction by the resilient connection of the upper springs 14 to the lower springs 15, and the displacement of the upper support plate 1 is recorded on the quick hardenable material by the front scribing needle 28 while forming a path for the movement of the lower jaw.

It is recommendable that a thin sheet of polyvinyl chloride is interposed between the upper and lower jaw models G and H in order to prevent both the upper and lower jaw models G and H, each made of gypsum, from being damaged or broken.

After the quick hardenable material is hardened in the fore receiving tray 16, it is subjected to mutual rubbing using a cinnabar seal ink in order to compensate the shrinkage of the quick hardenable material and then smoothly displace the front scribing needle 28 in conformity with the guidance path for the movement of the lower jaw.

When it is confirmed that the fore scribing needle 28 can move in the forward direction as well as in the leftward/rightward direction while the upper jaw model G is exactly aligned with the lower jaw model H for assuring correct central occlusion, each of the rear receiving trays 17 and 18 is filled with a quick hardenable material.

Next, movement of the upper and lower jaw models G and H in the forward direction as well as in the leftward/rightward direction is recorded on the quick hardenable materials in the rear receiving trays 17 and 18 by both the rear scribing needles 17 and 18 in cooperation with the guidance along the path for the movement of the lower jaw model H on the quick hardenable material in the front receiving tray 16, whereby another path for the movement of the lower jaw are formed on the quick hardenable materials on both of the rear receiving trays 17 and 18. After the quick hardenable materials in the rear receiving trays 17 and 18 are hardened in the same manner as that in the fore receiving tray 16, they are subjected to mutual rubbing using a cinnabar seal ink in order to compensate the shrinkage of the hardened materials and smoothly displace the rear scribing needles 30 and 31 in conformity with the guiding paths for the movement of the rear scribing needles 30 and 31 formed based on the results derived from the recording on the quick hardenable materials in the rear receiving trays 17 and 18.

It is recommendable that the paths for the movement of both the rear scribing needles 30 and 31 are previously marked using a pencil in order to prevent the foregoing paths formed based on the results derived from the recording on the quick hardenable materials in the rear receiving trays 17 and 18 from disappearing.

Next, when artificial teeth are inserted into damaged or broken parts on the upper and lower jaw models G and H and the paths for the movement of the lower jaw formed on the quick hardenable material are then followed by both the rear scribing needles 30 and 31, the patient's actual occlusion movement is reproduced, causing collision marks to appear on the incorrect spots of the artificial teeth. Thereafter, when a dentist exactly scrapes the collision marks on the artificial teeth, the artificial teeth completely suitable for the patient can be obtained.

Next, a position determination setting apparatus for setting a center line of an upper jaw in the form of an upper jaw model to a correct position in accordance with another embodiment of the present invention will be described below with reference to FIG. 4 to FIG. 7 which it is employable for the lower movement function readjusting apparatus constructed in the above-described manner in accordance with the first embodiment of the present invention.

The position determination setting apparatus is composed of a position determining unit 41 and an occlusion plane plate 42. The position determining unit 41 is constructed such that vertical walls 44 extend downward of the non-parallel opposite sides of a trapezoidal placement plate 43 (see FIG. 7), lower engagement pieces 45 adapted to be engaged with the lower surfaces of the lower spring support pipes 6 are bent inward of the lower ends of the vertical walls 44, and key-shaped engagement pieces 46 and 46' are formed at the front and rear parts of the vertical walls 44 while extending at a right angle relative to the latter so as to be fitted to the lower spring support pipes 6 placed on the lower support plate 2. On the other hand, the occlusion plane plate 42 is constructed such that cutouts 50 and 50' are formed on opposite sides of a substantially W-shaped plane plate 49, two separate tongue pieces 51 and 51' are disposed at the central part of the plane plate 49, and two parallel connection pieces 52 and 53 are bridged between the foremost ends of the tongue pieces 51 and 51' while a groove 54 is formed between the connection pieces 52 and 53. Modeling compounds 55 and 55' each having a thickness of about 1 mm are deposited on the tongue pieces 51 and 51' and then subjected to baking. It should be added the modeling compounds 55 and 55' have a length substantially corresponding to patient's Nos. 4 to 7 teeth.

Figure 6:
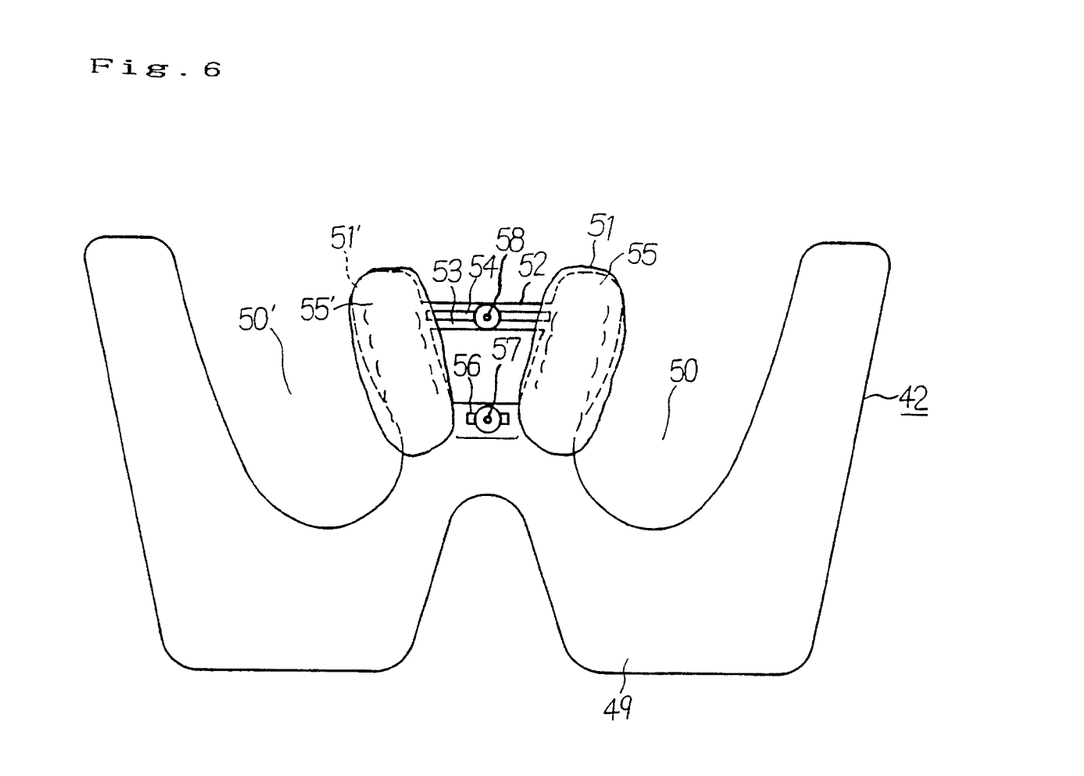
FIG. 6 is a plan view of an occlusion plane plate.

Occlusion planes corresponding to the patient's Nos. 4 to 7 teeth on his upper jaw are shallowly impressed on the modeling compounds 55 and 55' by the foregoing teeth. Subsequently, front and rear guide pins 57 and 58 are secured to the plane plate 49 in such a manner that they vertically project through the groove 54 between both the connection pieces 52 and 53 and another groove 56 formed in the vicinity of the terminal ends of the tongue pieces 51 and 51' while they are located at the central position between the opposite impressions on the modeling compounds 55 and 55'.

It should be noted that the fore guide pin 57 is dimensioned to have a shorter length and the rear guide pin 58 is dimensioned to have a longer length, that a stopper 59 having a relatively large diameter is disposed at the central part of each of the front and rear guide pins 57 and 58 so as to prevent the latter from being disconnected from the grooves 54 and 56, and that a lock nut 60 is threadably mounted on a male-threaded part of each of the fore and rear guide pins 57 and 58 while the lower end parts of the latter are projected downward of the lock nuts 60.

Figure 7:
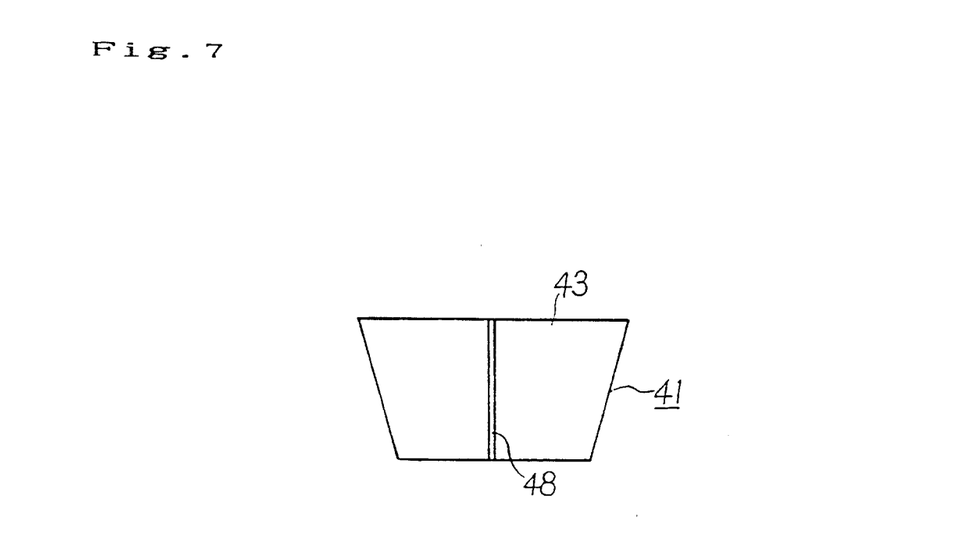
FIG. 7 is a plan view of a position determining unit operable in cooperation with the occlusion plane plate.

With the occlusion plane plate 42 constructed in the above-described manner, fitting portions 47 of the position determining unit 41 are fitted to the lower spring support tubes 6 on the lower support plate 2 so as to come in engagement with the reinforcement bars 9, and after the positions of the fitting portions 47 are properly determined, the downwardly projected parts of the front and rear guide pins 57 and 58 are fitted into a guide groove 48 on the placement plate 43 to determine the central position of the occlusion plane plate 42. Thereafter, the upper jaw model G is brought in engagement with the modeling compounds 55 and 55' so that the upwardly projected parts of the front and rear guide pins 57 and 58 are correctly aligned with the median seam line of the upper jaw model G, whereby the upper jaw model G is fixedly suspended from the upper support plate 1 via the mounting anvil 37.

After the upper jaw model G is fixedly held in that way, the lower jaw model H is caused to come in occlusive contact with the upper jaw model G so that it is fixedly mounted on the lower support plate 2. Consequently, the upper and lower jaw models G and H can be immovably be held at the exact positions.

Figure 8:
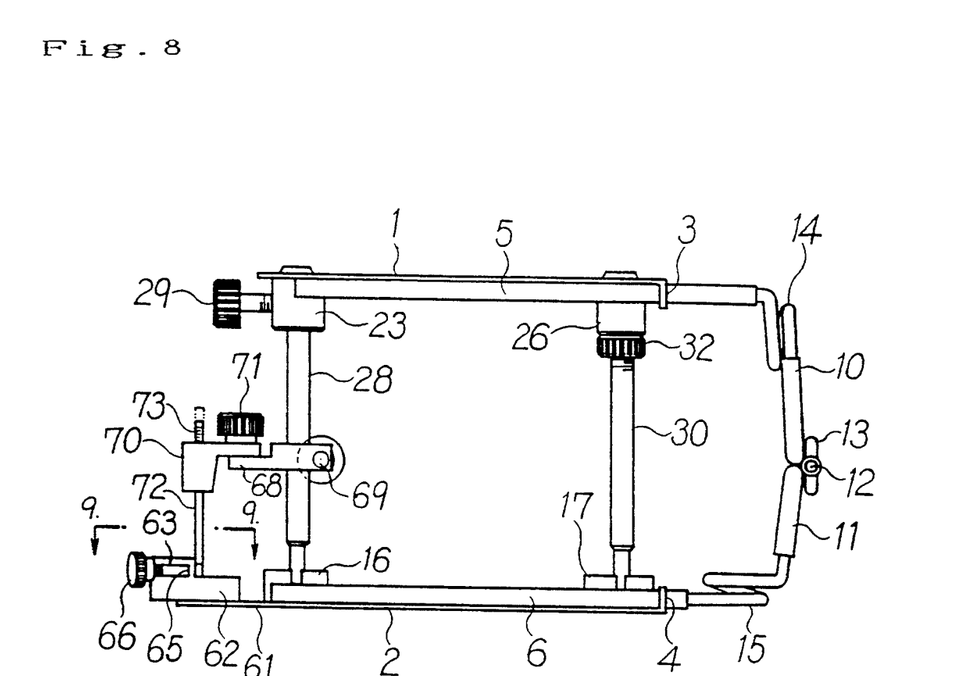
FIG. 8 is a side view of a lower jaw moving function readjusting apparatus in accordance with a second embodiment of the present invention.
Figure 9:
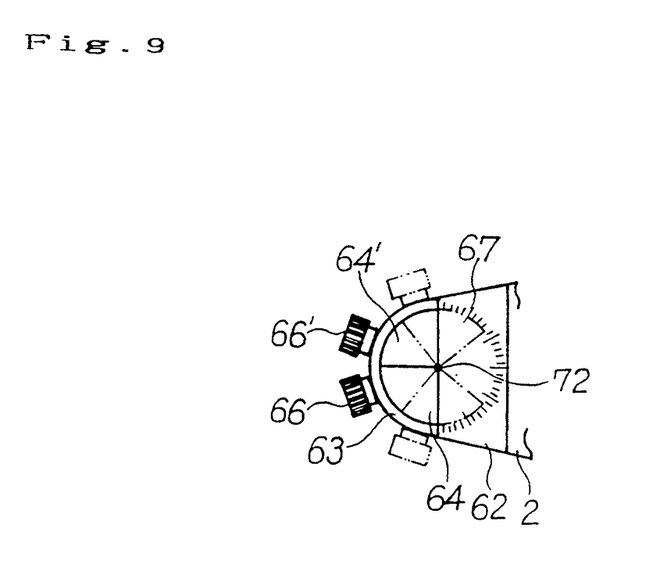
FIG. 9 is a fragmentary plan view of the lower jaw moving function readjusting apparatus shown in FIG. 8, particularly illustrating an adjustment board in a view taken along line 9—9 in FIG. 8.

Next, a lower jaw moving function readjusting apparatus in accordance with a second embodiment of the present invention will be described below with reference to FIG. 8 and FIG. 9. In this embodiment, same components as those in the first embodiment are represented by the same reference numerals. Thus, only components additionally arranged for the apparatus will be described below.

The lower support plate 2 has an extension from the foremost end thereof in the form of a mounting portion 61, and an adjusting board 62 is fixedly mounted on the upper surface of the mounting portion 61. An arc-shaped guide wall 63 is placed on the fore end side of the adjustment board 62, and two sector-shaped adjustment pieces 64 and 64' are arranged inside of the guide wall 63 (see FIG. 9). A guide groove 65 is formed on the side surface of the guide wall 63, and two male-threaded fixing rods 66 and 66' are inserted through the guide groove 65 until they are threadably engaged with the adjustment pieces 64 and 64'.

A series of calibrations 67 are formed along a semicircle on the upper surface of the adjustment board 62 on the opposite side to the guide wall 63.

The front scribing needle 28 employed for practicing the first embodiment of the present invention includes a holding piece 68 having a slit formed thereon at the intermediate position as seen in the direction of a height thereof, and a male-threaded fixing screw 69 is threadably engaged with the holding piece 68 through the foregoing slit so as to adjust the height and the position of the holding piece 68 adapted to turn in the leftward/rightward direction as desired. After completion of the adjustment, the holding piece 68 is fixedly secured to the fore scribing needle 28 by tightening the screw 69. A position determining piece 70 is placed at the foremost end of the holding piece 68, and after the position of the position determining piece 68 relative to the holding piece 68 as seen in the leftward/rightward direction is determined, the position determining piece 70 is fixedly secured to the holding piece 68 by tightening a male-threaded fixing screw 71. A position determining rod 72 is suspended from the position determining piece 70 so as to allow it to be normally biased in the downward direction by the resilient force of a spring (not shown). A plurality of horizontal calibrations 73 are formed at the upper end part of the position determining rod 72.

Other components rather than the aforementioned ones are same to those in the first embodiment of the present invention and they are designated by same reference numerals. Thus, further description on them will not be required.

In the second embodiment, since the apparatus is constructed in the above-described manner, means for mounting the upper and lower jaw models G and H, means for displacing the upper support plate 1 in the forward direction as well as in the leftward/rightward direction and means for forming a path for the movement of the lower jaw on the surface of a quick hardenable material filled in the receiving trays 16, 17 and 18 the same as those in the first embodiment of the present invention.

In the second embodiment, as the upper support plate 1 is displaced in the leftward/rightward direction, the position determining rod 72 is correspondingly displaced in the leftward/rightward direction. At this time, the sector-shaped adjustment pieces 64 and 64' are displaced so as to come in contact with the position determining rod 72, and after they are fixedly held on the adjustment board 62 by actuating the fixing rods 66 and 66', the positions where the adjustment pieces 64 and 64' are fixedly held in this manner are visually read along a series of calibrations 67. For example, when it is assumed that the adjustment piece 64' is displaced corresponding to the position of the correctly located adjustment piece 64 and then fixedly held on the adjustment board 62, both the adjustment pieces 64 and 64' can be displaced in the leftward/rightward direction symmetrically relative to each other, and moreover, the path for the movement of the lower jaw on the quick hardenable material can be properly adjusted.

When the position determining rod 72 is displaced in the upward/downward direction in the course of forward displacement of the upper support plate 1, the displacement of the position determining rod 72 is visually read with reference to the calibrations 73 so that the height of the position determining rod 72 as seen in the direction of visual reading can be adjusted properly.

According to the present invention, since the lower jaw moving readjustment apparatus is constructed and operates in the above-described manner, the upper support plate can freely be displaced by the upper springs in cooperation with the lower springs. Thus, when it is assumed that displacement of the upper support plate in the leftward/rightward direction is limitatively achieved within the positional range defined before a rounded part of a cusp on the upper functional zigomatic jaw, the bucal-lingual at the upper and lower non-support ends (representing horizontal overlap of the upper jaw relative to the lower jaw) is inevitably determined at the position having an extra positional quantity of about 0.5 mm in terms of the horizontal overlap of the cusp on the lower zigomatic jaw side. This contributes to easy preparation of each model and proper detection of any incorrect horizontal overlap. In addition, when it is assumed that the displacement of the upper support plate in the forward direction is limitatively achieved within the positional range defined by the position where Nos. 1 and 2 teeth on the left-hand/right-hand side of the upper jaw are brought in occlusive contact with those of the lower jaw, the horizontal overlap of fore-teeth on the upper jaw relative to those on the lower jaw as well as the position of an incisal edge can be determined, resulting in the user's requirement for excellent aesthetical feeling with the apparatus being satisfied.

Since upper and lower teeth can visually be observed without excessive separation of the upper teeth from the lower teeth, any incorrect separation therebetween can be detected.

In addition, since any complicated movement of the lower jaw can be three-dimensionally expressed depending on a magnitude of user's muscular power, the shapes of each functional cusp and functional fossa and the timing relationship of each occlusive contact can be determined correctly.

Movement of the lower jaw during masticating movement can be reproduced by displacing the lower jaw, and moreover, it is possible to prepare artificial teeth each having a high masticating efficiency by evenly opening the space between occlusion surfaces.

Since the models on the upper and lower jaws can be exactly located by using the position determining unit and the occlusion plane plate with the median seal line on the upper jaw as a reference for a median line extending on a cranium, a row of teeth can functionally be analyzed.

The direction of movement of the upper support plate is determined symmetrically relative to the median line by using the position determining rod. This makes it possible to properly grow jaw joints, and moreover, continuously maintain and quickly restore a normal function for a mouth system inclusive of a row of teeth, jaw bones and muscular nerves especially when the patient is an infant

What is claimed as new and is desired to be secured by Letters Patent of the United States is:

1. A lower jaw moving function readjusting apparatus, which comprises:
    an upper and lower triangular shaped support plate;
    a front receiving tray and two rear receiving trays fixedly mounted on said lower triangular shaped plate, each of said trays having a hardenable material located therein,
    a front scribing needle and two rear scribing needles, each of which has a lower end which is positioned in said hardenable material located in each of said front and rear receiving trays, said needles being suspended from said upper support plate wherein the height of at least one of said needles is adjustable, and
    upper springs and lower springs which are hinged together so as to be pivotably opened or closed wherein said upper springs and lower springs are secured, respectively, to said upper and lower support plates.

2. A lower jaw moving function readjusting apparatus as claimed in claim 1, which comprises:
    an upper substantially U-shaped spring joint tube with an upper side which is open and an inverted substantially U-shape spring joint tube with a lower side which is open wherein said upper joint tube and said inverted joint tube are pivotably secured to said hinge, one end of each of said upper springs has a single vertical turn fitted into an opposite end of said one end of said upper spring joint tube and each other end of said upper springs is held by said upper support plate on opposing sides of said upper support plate, and wherein one end of each of said lower springs has a single horizontal turn fitted into opposing ends of said lower spring joint tube and each other end of said lower springs is held by said lower support plate at opposing ends of said lower support plate.

3. A lower jaw moving function readjusting apparatus as claimed in claim 2 wherein each of said upper and lower support plates has a substantially triangular contour.

4. A lower jaw moving function readjusting apparatus as claimed in claims 2 or 3, which comprises:
    an arc-shaped guide wall which is projected forward of said front receiving tray located at the front end part of said lower support plate,
    an adjustment board having a series of calibrations formed along an arc portion of said board wherein said adjustment board is disposed on the front receiving tray side of said lower support plate,
    two sector-shaped adjustment pieces positioned so as to be movable along said guide wall and then fixedly secured to said guide wall,
    a holding piece mounted on said front scribing needle, and
    a position determining rod biased in a downward direction by a resilient force of a spring and having a plurality of calibrations formed at an upper end part of said rod, wherein said rod is suspended from said holding piece such that a lower end of said rod is brought into contract with said adjustment board while the position of said rod is adjustable on said adjustment board in an upward/downward direction as well as in a leftward/rightward direction.

5. A lower jaw moving function readjusting apparatus as claimed in claims 1, 2 or 3 which comprises a position determining setting apparatus which includes:
    a position determining unit having an upper surface with a trapezoidal contour and an occlusion plane plate positioned above said position determining unit wherein said position determining unit has a central guide groove formed thereon which extends between opposite parallel sides of said trapezoidal contour and includes fitting portions and key shaped engagement pieces fitted to said lower spring support tube on said lower support plate,
    said occlusion plane plate including a pair of tongue pieces for having a modeling compound deposited thereon, each of said tongue pieces including a plurality of impressions formed thereon corresponding to teeth of an upper jaw adapted to come in occlusive contact with teeth of said upper jaw model and two front and rear guide pins, the lower ends of which are fitted into said central guide groove and wherein ends of said front and rear guide pins project upwardly from said occlusion plane plate in alignment with a median seam line on said upper jaw model so as to allow said front and rear guide pins to be located at central portions between said impressions formed on the deposited modeling compounds.

6. A lower jaw moving function readjusting apparatus as claimed in claim 5, which comprises:
    two connecting pieces bridged between said tongue pieces on said occlusion plane plate which form a groove therebetween wherein terminal ends of said tongue pieces form a second groove therebetween,
    a stopper disposed at an intermediate portion of the length of each of said front and rear guide pins so as to allow said stopper to be placed on each of said grooves wherein one of said front and rear guide pins is fitted into each of the first and second grooves, and
    a lock nut is threadably engaged with male-threaded portions of each of said front and rear guide pins.

* * * * *